United States Patent [19]

Sirrenberg et al.

[11] Patent Number: 4,853,397
[45] Date of Patent: Aug. 1, 1989

[54] SUBSTITUTED FURAZANS AND INSECTICIDAL AND ACARICIDAL USE

[75] Inventors: Wilhelm Sirrenberg, Sprockhövel; Albrecht Marhold, Leverkusen; Robert Steffens, Cologne, all of Fed. Rep. of Germany

[73] Assignee: Bayer Aktiengesellschaft, Leverkusen, Fed. Rep. of Germany

[21] Appl. No.: 66,920

[22] Filed: Jun. 25, 1987

[30] Foreign Application Priority Data

Jul. 8, 1986 [DE] Fed. Rep. of Germany ....... 3622862

[51] Int. Cl.⁴ .................... A01N 43/82; C07D 273/02
[52] U.S. Cl. .................................... 514/364; 548/125; 558/17; 560/358; 564/307; 568/928
[58] Field of Search .......................... 548/125; 514/364

[56] References Cited

U.S. PATENT DOCUMENTS 4,369,186  7/1983  Beck et al. ..................... 514/354

FOREIGN PATENT DOCUMENTS 0002620  6/1979  European Pat. Off.
0132680  2/1985
3326509  1/1985  Fed. Rep. of Germany ...... 548/125
3409887  9/1985  Fed. Rep. of Germany ...... 548/125
3501723  7/1986  Fed. Rep. of Germany ...... 548/125

OTHER PUBLICATIONS

Malcauso et al, Heterocyclic rearrangements, tetrocycles, vol. 24 (#12) 1986, pp. 433-439.

Primary Examiner—Richard L. Raymond
Attorney, Agent, or Firm—Sprung Horn Kramer & Woods

[57] ABSTRACT

Insecticidal and acaricidal novel substituted furazans of the formula

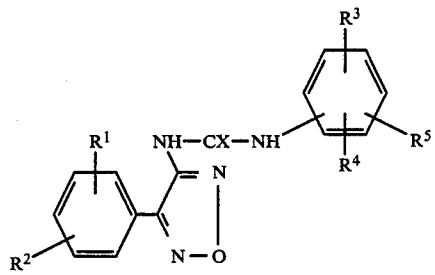

n which
$R^1$ and $R^2$ are identical or different and represent hydrogen, halogen, alkyl, alkoxy, alkylthio, halogenoalkyl, halogenoalkoxy, halogenoalkylthio or optionally substituted aryloxy, or
$R^1$ and $R^2$ together represent an optionally substituted alkylene radical which is interrupted by 1 or 2 oxygen atoms or is bonded to the phenyl radical via 1 or 2 oxygen atoms,
$R^3$ and $R^4$ are identical or different and represent hydrogen, halogen, alkyl, alkoxy, halogenoalkyl or halogenoalkoxy,
$R^5$ represents optionally substituted cycloalkyl, and
X represents oxygen or sulphur.

Intermediates of the formula

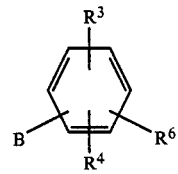

in which
B is $-NH_2$, $-NO_2$ or $-NCX$,
$R^3$ and $R^4$ are identical or different and represent hydrogen, halogen, alkyl, alkoxy, halogenoalkyl or halogenoalkoxy,
$R^6$ represents 2,2-difluoro-1-methylcycloprop-1-yl or the

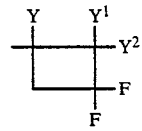

radical,
Y represents hydrogen, methyl, fluorine or chlorine, and
$Y^1$ and $Y^2$ are identical or different and represent fluorine or chlorine,
are also new.

9 Claims, No Drawings

SUBSTITUTED FURAZANS AND INSECTICIDAL AND ACARICIDAL USE

The invention relates to new substituted furazans, processes for the preparation thereof, and the use thereof as pesticides, particularly as insecticides and acaricides.

It is hitherto known that substituted furazans, such as, for example, 1-(4-tert.-butylphenyl)-3-[4-(4-chlorophenyl)-1,2,5-oxadiazol-3-yl]-urea, 1-(4-trifluoromethylphenyl)-3-(4-phenyl-1,2,5-oxadiazol-3-yl)-urea and 1-(4-bromophenyl)-3-(4-phenyl-1,2,5-oxadiazol-3-yl)-urea, have insecticidal and acaricidal properties (cf. EP-A 132,680).

The new substituted furazans of the formula (1)

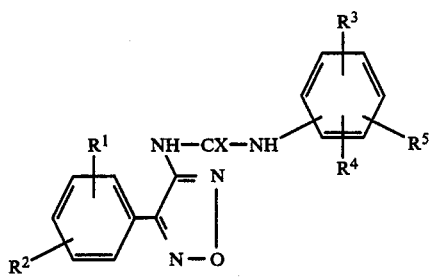

in which
$R^1$ and $R^2$ are identical or different and represent hydrogen, halogen, alkyl, alkoxy, alkylthio, halogenoalkyl, halogenoalkoxy, halogenoalkylthio or optionally substituted aryloxy, or
$R^1$ and $R^2$ together represent an optionally substituted alkylene radical which is interrupted by 1 or 2 oxygen atoms or is bonded to the phenyl radical via 1 or 2 oxygen atoms,
$R^3$ and $R^4$ are identical or different and represent hydrogen, halogen, alkyl, alkoxy, halogenoalkyl or halogenoalkoxy,
$R^5$ represents optionally substituted cycloalkyl, and
X represents oxygen or sulphur,
have now been found.

It has furthermore been found that the new substituted furazans of the formula (I) are obtained by (a) reacting 3-amino-1,2,5-oxadiazoles of the formula (II)

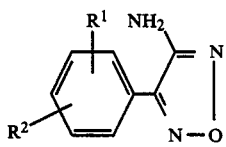

in which
$R^1$ and $R^2$ have the abovementioned meanings,
with iso(thio)cyanates of the formula (III)

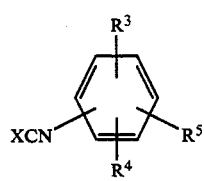

in which
X, $R^3$, $R^4$ and $R^5$ have the abovementioned meanings, if appropriate in the presence of catalysts and if appropriate in the presence of diluents, or (b) reacting 3-iso(thio)cyanato-1,2,5-oxadiazoles of the formula (IV)

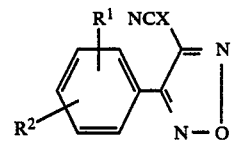

in which
X, $R^1$ and $R^2$ have the abovementioned meanings, with anilines of the formula (V)

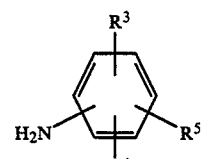

in which
$R^3$, $R^4$ and $R^5$ have the abovementioned meanings, if appropriate in the presence of catalysts and if appropriate in the presence of diluents.

The compounds of the formula (I) may be present in various geometrical and optical isomeric forms, depending on the arrangement of the substituents which are bonded to the cycloalkyl radical; they are preferably produced in a varying isomeric ratio. The present invention relates both to the individual isomers and to the isomeric mixtures.

Alkyl $R^1$, $R^2$, $R^3$ and $R^4$ is straight-chain or branched and preferably contains 1 to 12, particularly preferably 1 to 6, in particular 1 to 4, carbon atoms.

Examples which may be mentioned are methyl, ethyl, n-propyl, i-propyl, n-butyl, i-butyl, sec.-butyl and tert.-butyl (preferably methyl).

Alkoxy $R^1$, $R^2$, $R^3$ and $R^4$ contain, in the alkyl part, straight-chain or branched alkyl preferably having 1 to 12, particularly preferably 1 to 6, in particular 1 to 4, carbon atoms.

Examples which may be mentioned are methoxy, ethoxy, n-propoxy, i-propoxy, n-butoxy, i-butoxy, sec.-butoxy and tert.-butoxy (preferably methoxy).

Alkylthio $R^1$ and $R^2$ contain, in the alkyl part, straight-chain or branched alkyl preferably having 1 to 6, in particular 1 to 4, carbon atoms.

Examples which may be mentioned are methylthio, ethylthio, n-propylthio, i-propylthio, n-butylthio, i-butylthio, sec.-butylthio and tert.-butylthio (preferably methylthio). Halogenoalkyl and halogenoalkoxy $R^1$, $R^2$, $R^3$ and $R^4$ and halogenoalkylthio $R^1$ and $R^2$ contain, in the alkyl part, straight-chain or branched alkyl preferably having 1 to 6, particularly preferably 1 to 4, in particular 1 to 2, carbon atoms and preferably 1 to 6, in particular 1 to 4, halogen atoms, the halogen atoms being identical or different and fluorine, chlorine or bromine, particularly fluorine, standing as halogen atoms.

Examples which may be mentioned are trifluoromethyl, chlorodifluoromethyl, difluoromethyl, trifluoromethylthio, chlorodifluoromethylthio, trifluoroethylthio, chlorotrifluoroethylthio, tetrafluoroethylthio, trifluoromethoxy, difluoromethoxy, tetrafluoroethoxy, chlorotrifluoroethoxy and bromotrifluoroethoxy (preferably trifluoromethyl and trifluoromethoxy).

Aryloxy preferably having 6 to 10 carbon atoms in the aryl part, in particular 6 carbon atoms in the aryl part, stands as optionally substituted aryloxy $R^1$ and $R^2$. Examples which may be mentioned are optionally substituted phenoxy or naphthyloxy (preferably phenoxy).

The optionally substituted aryloxy radicals $R^1$ and $R^2$ may carry one or more, preferably 1 to 3, in particular 1 or 2, identical or different substituents.

Examples which may be listed as aryl substituents are: halogen, preferably fluorine, chlorine, bromine or iodine, in particular chlorine and bromine; cyano; nitro; alkyl preferably having 1 to 4, in particular 1 or 2, carbon atoms, such as methyl, ethyl, n-and i-propyl and n-, i-, sec.- and tert.-butyl; alkoxy preferably having 1 to 4, in particular 1 or 2, carbon atoms, such as methoxy, ethoxy, n- and i-propyloxy and n-, i-, sec.- and tert.-butyloxy; alkylthio preferably having 1 to 4, in particular 1 or 2, carbon atoms, such as methylthio, ethylthio, n- and i-propylthio and n-, i-, sec.- and tert.-butylthio; halogenalkyl, halogenoalkoxy and halogenalkylthio in each case preferably having 1 to 4, in particular 1 or 2, carbon atoms and preferably 1 to 5, in particular 1 to 3, halogen atoms, the halogen atoms being identical or different and fluorine, chlorine or bromine, particularly fluorine, preferably standing as halogen atoms, such as trifluoromethyl, trifluoromethoxy and trifluoromethylthio. Preferred substituents are trifluoromethyl and chlorine.

In the definition of $R^1$ and R2, optionally substituted alkylene, which is interrupted by 1 or 2 oxygen atoms or (preferably) bonded to the phenyl ring via 1 or 2 oxygen atoms, preferably contains 1 to 3, in particular 1 or 2, carbon atoms and may be substituted by $C_1$-$C_4$-alkyl and/or halogen. Examples which may be mentioned are: —O—CF$_2$CClF—O—, —O—CH$_2$—O— and —CH$_2$—O—CH$_2$—O—.

Cycloalkyl preferably having 3 to 8 carbon atoms, in particular 3 to 6 carbon atoms, in the cycloalkyl ring stands as optionally substituted cycloalkyl $R^5$. Optionally substituted cyclopropyl, cyclobutyl, cyclopentyl or cyclohexyl may be mentioned as examples.

The optionally substituted cycloalkyl radical $R^5$ may carry one or more, preferably 1 to 7, in particular 3, 4 or 5, identical or different substitutents. Examples which may be listed as substituents for $R^5$ are: halogen, preferably fluorine, chlorine, bromine or iodine, in particular fluorine and chlorine; alkyl preferably having 1 or 2 carbon atoms, such as methyl or ethyl, in particular methyl.

Unless otherwise stated, halogen represents fluorine, chlorine, bromine and iodine, preferably chlorine and fluorine, it being possible for the halogen atoms in each case to be identical or different.

$R^1$ and $R^2$ preferably represent hydrogen, fluorine and/or chlorine.

The radicals $R^1$ and $R^2$ are preferably in the 2-, 4-, 2,4-, 3,4- or 2,6-position of the phenyl ring.

The radicals $R^3$ and $R^4$ preferably represent hydrogen.

The radical $R^5$ preferably represents substituted cyclopropyl and cyclobutyl, with methyl, fluorine and/or chlorine preferably standing as substituents.

$R^5$ preferably represents 2,2-difluoro-1-methyl-cyclopropyl-1-yl or the radical

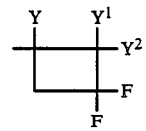

in which

Y represents hydrogen, methyl, fluorine or chlorine, and $Y^1$ and $Y^2$ are identical or different and represent fluorine or chlorine.

$R^5$ particularly preferably represents 2-chloro-2,3,3-trifluorocyclobutyl (Y=H, $Y^1$=Cl, $Y^2$=F), 2-chloro-1-methyl-2,3,3-trifluorocyclobutyl (Y=CH$_3$, $Y^1$=Cl, $Y^2$=F) or 2,2,3,3-tetrafluoro-cyclobutyl (Y=H, $Y^1$ and $Y^2$=F).

In the general formulae (I), (III) and (V), the radical $R^5$ in the phenyl ring is preferably in the 4-position to the —NH—, —NH$_2$ or —NCX group.

X preferably denotes oxygen.

The new compounds of the formula (I) have properties which make possible their use as pesticides, in particular they are distinguished by an excellent insecticidal and acaricidal action.

Preferred new substituted furazans of the formula (I) are those in which $R^1$ and $R^2$ are identical or different and represent hydrogen, halogen, $C_1$-$C_6$-alkyl, $C_1$-$C_6$-alkoxy, $C_1$-$C_6$-alkylthio, halogeno-$C_1$-$C_6$-alkyl, halogeno-$C_1$-$C_6$-alkoxy, halogeno-$C_1$-$C_6$-alkylthio or aryloxy, having 6 to 10 carbon atoms in the aryl part, which is optionally substituted by halogen, nitro, cyano, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy and/or halogeno-$C_1$-$C_4$-alkylthio, or $R^1$ and $R^2$ together represent a $C_1$-$C_3$-alkylene radical which is interrupted by 1 or 2 oxygen atoms or bonded to the phenyl ring via 1 or 2 oxygen atoms and which is optionally substituted by halogen and/or $C_1$-$C_2$-alkyl, $R^3$ and $R^4$ are identical or different and represent hydrogen, halogen, $C_1$-$C_6$-alkyl, $C_1$-$C_6$-alkoxy, halogeno-$C_1$-$C_6$-alkyl or halogeno-$C_1$-$C_4$-alkoxy, $R^5$ represents cycloalkyl, having 3 to 8 carbon atoms, which is optionally substituted by halogen and/or $C_1$-$C_2$-alkyl, and X represents oxygen or sulphur.

Particularly preferred new substituted furazans of the formula (I) are those in which $R^1$ and $R^2$ are identical or different and represent hydrogen, fluorine, chlorine, bromine, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy, halogeno-$C_1$-$C_4$-alkylthio or phenoxy which is optionally substituted by halogen, nitro, cyano, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy and/or halogeno-$C_1$-$C_4$-alkylthio, or $R^1$ and $R^2$ together represent a $C_1$-$C_3$-alkylene radical which is interrupted by 1 or 2 oxygen atoms or bonded to the phenyl ring vis 1 or 2 oxygen atoms and which is optionally substituted by flourine, chlorine and/or methyl, $R^3$ and $R^4$ are identical or different and represent hydrogen, fluorine, chlorine, bromine, $C_1$-$C_4$- alkyl, $C_1$-$C_4$-alkyl, $C_1$-$C_4$-alkoxy, halogeno-$C_1$-$C_4$-alkyl or halogeno-$C_1$-$C_4$-alkoxy, $R^5$ represents cycloalkyl, having 3 to 6 carbon atoms, which is optionally substituted by fluorine, chlorine, bromine, and/or methyl, and X represents oxygen or sulphur.

Very particularly preferred new substituted furazans of the formula (I) are those in which $R^1$ and $R^2$ are identical or different and represent hydrogen, fluorine, chlorine, bromine, methoxy, ethoxy, methyl, ethyl, n-propyl, i-propyl, n-butyl, i-butyl, sec.-butyl, sec.-butyl, tert.-butyl, methylthio, ethylthio, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio, hexafluoropropylthio, or phenoxy which is optionally substituted by fluorine, chlorine, bromine, nitro, cyano, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio and/or hexafluoropropylthio, or $R^1$ and $R^2$ together represent difluoromethylenedioxy, ethylenedioxy, chlorotrifluoroethylenedioxy, difluoroethylenedioxy, methylenedioxy, trifluoroethylenedioxy, difluoromethyleneoxydifluoromethyleneoxy, tetrafluoroethylenedioxy, 2-methyl-1,1,2-trifluoroethylenedioxy or 2,2-dimethylethyleneoxy, $R^3$ and $R^4$ are identical or different and represent hydrogen, fluorine, chlorine, bromine, methyl, ethyl, n-propyl, i-propyl, n-butyl, i-butyl, sec.-butyl, tert.-butyl, methoxy, ethoxy, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy or hexafluoropropoxy, $R^5$ represents cyclopropyl, cyclobutyl, cyclopentyl or cyclohexyl which are optionally substituted by fluorine, chlorine, bromine and/or methyl, and X represents oxygen or sulphur.

Of particular interest are those compounds of the formula (I) in which $R^1$ and $R^2$ are identical or different and represent hydrogen, fluorine, chlorine, bromine, methyl, methoxy, methylthio, trifluoromethyl, trifluoromethoxy, trifluoromethylthio or phenoxy which is optionally substituted by chlorine, methyl, methoxy, methylthio, trifluoromethyl, trifluoromethoxy and/or trifluoromethylthio, or $R^1$ and $R^2$ together represent methylenedioxy, ethylenedioxy, difluoromethylenedioxy, tetrafluoroethylenedioxy or chlorotrifluoroethylenedioxy, $R^3$ and $R^4$ are identical and represent hydrogen, $R^5$ represents cyclopropyl or cyclobutyl which are substituted by fluorine, chlorine, and/or methyl, and X represents oxygen or sulphur.

Of very particular interest are those compounds of the formula (I) in which $R^1$ and $R^2$ are identical or different and represent hydrogen, fluorine or chlorine, $R^2$ and $R^3$ represent hydrogen, $R^5$ represents 2-chloro-2,3,3-trifluorocyclobutyl, 1-methyl-2-chloro-2,3,3-trifluorocyclobutyl or 2,2,3,3-tetrafluorocyclobutyl and X represents oxygen or sulphur (preferably oxygen).

If 3-amino-4-(4-chlorophenyl)-1,2,5-oxadiazole and 4-(2,2,3,3-tetrafluoro-cyclobut-1-yl)-phenyl isocyanate are used as starting materials according to process version (a), then the course of the reaction may be represented by the following equation:

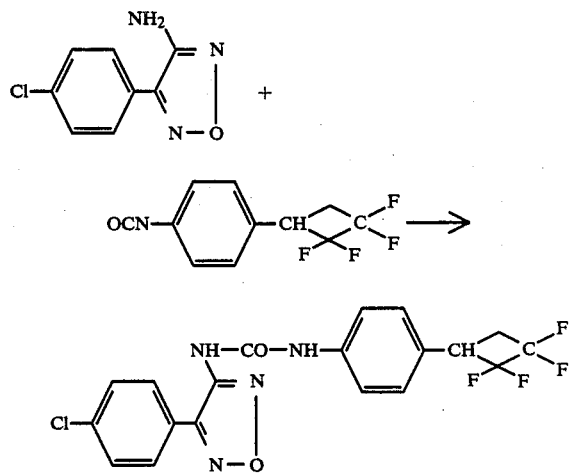

I 4-(4-chlorophenyl)-3-isocyanato-1,2,5-oxadiazole and 4-(2-chloro-1-methyl-2,3,3-trifluoro-cyclobut-1-yl)-aniline are used as starting materials according to process version (b), then the course of the reaction may be represented by the following equation:

The 3-amino-1,2,5-oxadiazoles of the formula (II) to be used as staring materials are known and/or may be prepared by processes and methods which are known from the literature (cf. J. Prakt. Chem. 315, 4, page 791–795 (1973)). The amino group may be converted into the isocyanate or iso-thio-cyanate group by conventional processes, for example by reaction with phosgene or thiophosgene in diluents such as, for example, toluene and/or pyridine, at a temperature between −20° C. and +50° C. The compounds of the formula (IV) are obtained in this fashion. Some of the compounds of the formulae (III) and (V) are known (cf., for example, J. Am. Chem. Soc. 93, 7208 ff. (1971) and Zh. Org. Khim. 10, 477–483 (1974)). The new compounds of the formulae (III) and (V) are described below.

Suitable diluents in the process according to the invention (versions (a) and (b)) are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and also tetramethylene sulphone.

Preferred catalysts for the reaction according to process versions (a) and (b) are tertiary amines, such as triethylamine, and 1,4-diazabicyclo-[2,2,2]-octane, and also organotin compounds, such as, for example, dibutyltin dilaurate. In general, the addition of the catalyst brings no advantages.

The reaction temperature may be varied within a relatively wide range. In general, the process version (a) is carried out at temperatures between 20° C. and 180° C., preferably between 40° C. and 120° C., and process version (b) is carried out at temperatures between 20° C. and 200° C., preferably between 60° C. and 190° C. The process versions according to the invention are generally carried out at atmospheric pressure.

To carry out the process versions according to the invention, the starting materials are usually employed in approximately equimolar amounts. An excess of either reaction component brings no significant advantages. 0.6 to 1.5 mols, in particular 0.8 to 1.2 mols, of the compound of the formula (III) or (V) are preferably employed per mol of the compounds of the formula (II) or (IV) respectively.

In reaction products are worked up by conventional methods, for example by filtering off the precipitated product under suction or by extracting undesired by-products from the reaction mixture. The melting point serves for characterization.

Some of the compounds of the formulae (III) and (V) are new. The new compounds may be summarized under the general formula (VI):

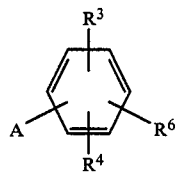

(VI)

in which

A represents —NH$_2$ or —NCX, where
X represents oxygen or sulphur,
R$^3$ and R$^4$ are identical or different and represent hydrogen, halogen, alkyl, alkoxy, halogenoalkyl or halogenoalkoxy, and
R$^6$ represents 2,2-difluoro-1-methyl-cycloprop-1-yl or the

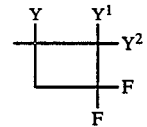

radical, in which
Y represents hydrogen, methyl, fluorine or chlorine, and
Y$^1$ and Y$^2$ are identical or different and represent fluorine or chlorine.

These compounds of the formula (VI) and the processes for the preparation thereof are part of the present invention.

The compounds of the general formula (VI) are obtained by reducing nitrobenzenes of the formula (VII)

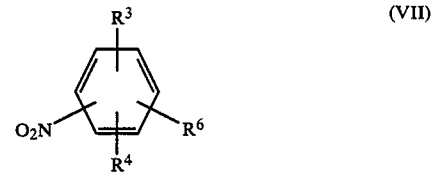

(VII)

in which
R$^3$ and R$^4$ are identical or different and represent hydrogen, halogen, alkyl, alkoxy, halogenoalkyl or halogenoalkoxy, and
R$^6$ represents 2,2-difluoro-1-methyl-cycloprop-1-yl or the

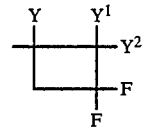

radical, in which
Y represents hydrogen, methyl, fluorine or chlorine, and
Y$^1$ and Y$^2$ are identical or different and represent fluorine or chlorine, in a conventional fashion, preferably by catalytic hydrogenation or with the aid of metals or metal salts, and, if appropriate, reacting the resultant amino compound with phosgene or thiophosgene.

All conventional catalysts, such as Raney nickel, platinum, platinum oxide and palladium, are suitable for the catalytic hydrogenation of the nitro compounds of the general formula (VII), it being possible for the catalysts to be present on supports, for example activated charcoal or aluminium oxide.

All solvents which are conventionally employed in hydrogenations are suitable as solvents, such as alcohols, for example methanol, or ethers, for example dioxane and tetrahydrofuran.

In general, increased hydrogen pressures, preferably between 10 and 80 bar, are employed. The hydrogenation is preferably carried out at temperatures from 10° C. to 100° C., particularly 20° C. to 80° C. The compounds of the general formula (VI) (A denotes —NH$_2$) or (V) are worked up and isolated in a conventional fashion.

The reduction of the nitro compounds of the general formula (VII) can also be carried out, in a conventional fashion, using metals, such as iron and tin and the salts thereof, preferably SnCl$_2$. The reduction using SnCl$_2$ is preferably carried out in a mixture of aqueous HCl and dioxane (or alternatively anhydrously in alcohols, such as ethanol) at temperatures between 20° C. and 100° C. Iron in the form of iron powder or iron turnings may also be used analogously, temperatures from 80° C. to 100° C. preferably being employed. The compounds of the general formula (VI) (A denotes —NH$_2$) or (V) are also worked up and isolated here in a conventional fashion.

The compounds of the general formula (VI) (A denotes —NCX) or (III) can easily be obtained from the compounds of the general formula (VI) (A denotes —NH$_2$) or (V) and phosgene or thiophosgene by the conventional phosgenation methods. Optionally halogenated aromatic or aliphatic solvents, such as chlorotoluene, toluene or xylene, are preferably used as solvents.

The phosgenation is preferably carried out at temperature between 0° C. and 150° C., particularly between 0° C. and 150° C.

The compounds of the general formula (VI) (A denotes —NCX) or (V) are generally worked up and isolated by conventional methods.

The compounds of the general formula (VII) are new. These compounds, and also the process for the preparation thereof, are likewise part of the present invention.

The compounds of the general formula (VII) are obtained by nitrating benzenes of the formula (VIII)

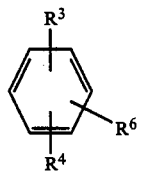

(VIII)

in which
R$^3$ and R$^4$ are identical or different and represent hydrogen, halogen, alkyl, alkoxy, halogenoalkyl or halogenoalkoxy, and
R$^6$ represents 2,2-difluoro-1-methyl-cycloprop-1-yl of the

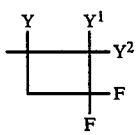

radical, in which
Y represents hydrogen, methyl, fluorine or chlorine, and
Y$^1$ and Y$^2$ are identical or different and represent fluorine or chlorine,
by generally conventional methods of nuclear nitration. The nitrating acid (mixture of concentrated sulphuric acid and concentrated nitric acid) is preferably added slowly to the compound of the general formula (VIII) at temperatures between 0° C. and 50° C., particularly between 5° C. and 40° C., without using a solvent, and the reaction mixture is kept at this temperature for 1 to 3 hours, and, if appropriate, a solvent, such as, for example, dichloromethane, is added towards the end of the reaction. The reaction mixture is subsequently poured onto ice, the desired product separating off as the organic phase and being easily separated off. The compounds of the formula (VII) are purified by conventional methods.

The compounds of the formula (VIII) are known and/or may be prepared by known processes (cf., for example, J. Am. Chem. Soc. 83, 382 (1961) and 86, 2645 (1964)).

The new compounds of the general formulae (VI) and (VII) may be summarized in the following general formula (IX):

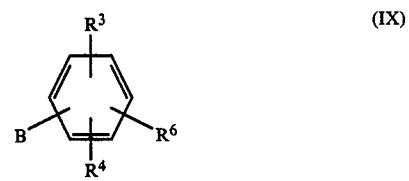

(IX)

in which
B represents —NH$_2$, —NO$_2$ or —NCX, in which
X represents oxygen or sulphur,
R$^3$ and R$^4$ are identical or different and represent hydrogen, halogen, alkyl, alkoxy, halogenoalkyl or halogenoalkoxy, and
R$^6$ represents 2,2-difluoro-1-methyl-cycloprop-1-yl or the

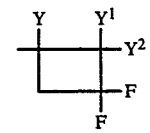

radical, in which
Y represents hydrogen, methyl, fluorine or chlorine, and
Y$^1$ and Y$^2$ are identical or different and represent fluorine or chlorine.

The preferred definitions and positions of the radicals in the compounds of the general formulae (II) to (V) and, with respect to the radicals R$^1$, R$^2$, R$^3$, R$^4$ and X, also in the compounds of the general formulae (VI) to (IX), corresponds to those which were specified above for the compounds of the general formula (I).

The active compounds are suitable for combating animal pests, preferably arthropods, in particular insects and arachnida, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.*
From the order of the Diplopoda, for example, *Blaniulus guttulatus.* From the order of the Chilopoda, for example, *Geophilus carpophagus* and *Scutigera* spec. From the order of the Symphyla, for example, *Scutige-*

*rella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimtobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia supp., *Bibio hortulanus,* Oscinella frit, Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds, according to the invention, of the formula (I) are distinguished by an excellent insecticidal and acaricidal action, preferably against eggs (ovicidal action) and the larvae (larvicidal action) of the pests. Particularly when used as acaricides, they exhibit an excellent development-inhibiting action on eggs and-/or larvae of Tetranychida, such as, for example, *Tetranychus urticae.* The active compounds according to the invention also exhibit a very good action when combating insects which damage plants, such as, for example, *Phaedon cochleariae* larvae.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates. The preparation of the compounds according to the invention and the biological activity of the compounds, according to the invention, of the formula (I) is described with reference to the following examples.

PREPARATION EXAMPLES

Example 1

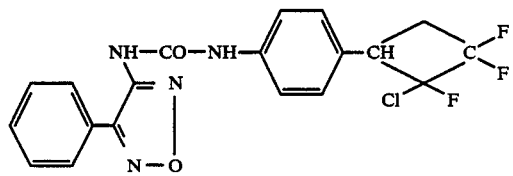

(Process version (b))

1.87 g (0.01 mol) of 3-isocyanato-4-phenyl-1,2,5-oxadiazole, dissolved in 10 ml of dry toluene, are added at 40° C. with exclusion of moisture to a solution of 2.36 g (0.01 mol) of 4-(2-chloro-2,3,3-trifluorocyclobutyl)-aniline in 40 ml of toluene.

The batch is stirred for half an hour at 80° C. and subsequently evaporated in vacuo. The precipitated product is filtered off under suction and washed with petroleum ether. 3.2 g (76% of theory) of 1-[4-(2-chloro-2,3,3-trifluorocyclobutyl)-phenyl]-3-(4-phenyl-1,2,5-oxadiazol-3-yl)-urea of melting point 201° C. are obtained.

The compounds of the formula (I) listed in Table 1 below are prepared analogously to Example 1 or process versions (a) or (b):

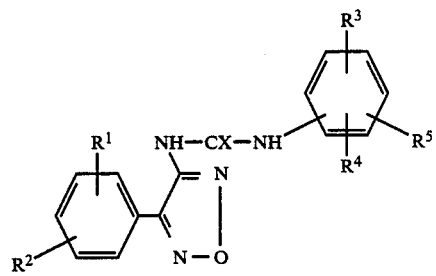

TABLE 1

| Example No. | $R^1$ | $R^2$ | $R^3$ | $R^4$ | $R^5$ | X | Melting point [°C.] |
|---|---|---|---|---|---|---|---|
| 2 | 4-Cl | H | H | H | 4—CH(cyclobutyl-CF₂-CClF) | O | 216 |
| 3 | 4-F₃C—C₆H₃(Cl)—O— | H | H | H | 4—CH(cyclobutyl-CF₂-CClF) | O | 114 |
| 4 | H | H | H | H | 4—CH(cyclobutyl-CF₂-CClF) | S | 112 |
| 5 | 4-F | H | H | H | 4—CH(cyclobutyl-CF₂-CClF) | O | 226 |

TABLE 1-continued

| Example No. | R¹ | R² | R³ | R⁴ | R⁵ | X | Melting point [°C.] |
|---|---|---|---|---|---|---|---|
| 6 | 4-Br | H | H | H | 4—CH(Cl)—CF₂—F (with CF₂F) | O | 221 |
| 7 | 2-F | 4-F | H | H | 4—CH(Cl)—CF₂F | O | 186 |
| 8 | 2-Cl | 4-CF₃ | H | H | 4—CH(Cl)—CF₂F | O | 203 |
| 9 | H | H | H | H | 4—CH(F)—CF₂F | O | 206–208 |
| 10 | 4-F | H | H | H | 4—CH(F)—CF₂F | O | 225 |
| 11 | 4-Br | H | H | H | 4—CH(F)—CF₂F | O | 248 |
| 12 | 4-Cl | H | H | H | 4—CH(F)—CF₂F | O | 232 |
| 13 | 4-CH₃ | H | H | H | 4—CH(F)—CF₂F | O | 223 |
| 14 | 3-Cl | 4-Cl | H | H | 4—CH(F)—CF₂F | O | 219 |
| 15 | 3,4-OCH₂O— | | H | H | 4—CH(F)—CF₂F | O | 195 |
| 16 | 4-CH₃O— | H | H | H | 4—CH(F)—CF₂F | O | 231 |
| 17 | 4-F₃C—C₆H₄—O— | H | H | H | 4—CH(F)—CF₂F | O | 189 |
| 18 | 4-F₃C-(2,6-Cl₂)C₆H₂—O— | H | H | H | 4—CH(F)—CF₂F | O | 203 |
| 19 | 4-F₃C-(2-Cl)C₆H₃—O— | H | H | H | 4—CH(F)—CF₂F | O | 109 |

TABLE 1-continued

| Example No. | R¹ | R² | R³ | R⁴ | R⁵ | X | Melting point [°C.] |
|---|---|---|---|---|---|---|---|
| 20 | H | H | H | H | 4-C(CH₃)(Cl)-C(F)₂-F | O | 202 |
| 21 | 4-F | H | H | H | 4-C(CH₃)(Cl)-C(F)₂-F | O | 210 |
| 22 | 4-Br | H | H | H | 4-C(CH₃)(Cl)-C(F)₂-F | O | 219 |
| 23 | H | H | H | H | 4-C(CH₃)(Cl)-C(F)₂-F | S | 146 |
| 24 | 4-Cl | H | H | H | 4-C(CH₃)(Cl)-C(F)₂-F | O | 222 |
| 25 | 2-Cl | H | H | H | 4-C(CH₃)(Cl)-C(F)₂-F | O | 222 |
| 26 | 2-Cl | 4-Cl | H | H | 4-C(CH₃)(Cl)-C(F)₂-F | O | 181 |
| 27 | 4-CF₃ | H | H | H | 4-C(CH₃)(Cl)-C(F)₂-F | O | 223 |
| 28 | 4-CF₃O— | H | H | H | 4-C(CH₃)(Cl)-C(F)₂-F | O | 229 |
| 29 | 4-CH₃ | H | H | H | 4-C(CH₃)(Cl)-C(F)₂-F | O | 199 |
| 30 | 4-CH₃O— | H | H | H | 4-C(CH₃)(Cl)-C(F)₂-F | O | 226 |
| 31 | 4-F₃C—C₆H₄—O— | H | H | H | 4-C(CH₃)(Cl)-C(F)₂-F | O | 102 |

TABLE 1-continued

| Example No. | R¹ | R² | R³ | R⁴ | R⁵ | X | Melting point [°C.] |
|---|---|---|---|---|---|---|---|
| 32 | 4-CF₃O— | | H | H | H | 4-C(CH₃)(Cl)-C(F)(F)-F | O | 228 |
| 33 | 4-Cl | | 3-Cl | H | H | 4-C(CH₃)(Cl)-C(F)(F)-F | O | 229 |
| 34 | | 3,4-OCH₂O— | | H | H | 4-C(CH₃)(Cl)-C(F)(F)-F | O | 180 |
| 35 | 4-Cl | | H | H | H | 4-C(CH₃)(F)-C(F)(CH₂) | O | 215 |
| 36 | 4-F | | H | H | H | 4-C(CH₃)(F)-C(F)(CH₂) | O | 210 |
| 37 | 4-Br | | H | H | H | 4-C(CH₃)(F)-C(F)(CH₂) | O | 211 |
| 38 | 4-CH₃ | | H | H | H | 4-C(CH₃)(F)-C(F)(CH₂) | O | 184 |
| 39 | 4-Cl | | 3-Cl | H | H | 4-C(CH₃)(F)-C(F)(CH₂) | O | 220 |
| 40 | | 3,4-O—CH₂—O— | | H | H | 4-C(CH₃)(F)-C(F)(CH₂) | O | 177 |
| 41 | | 4-F₃C—C₆H₄—O— | | H | H | 4-C(CH₃)(F)-C(F)(CH₂) | O | 101 |
| 42 | H | | H | H | H | 2-CH-C(F)(F)-CF₂ | O | 184 |
| 43 | 4-F | | H | H | H | 2-CH-C(F)(F)-CF₂ | O | 195 |
| 44 | H | | H | H | 3-CF₃ | 4-CH-C(F)(F)-CF(Cl) | O | 210 |
| 45 | 4-Cl | | H | H | 3-CF₃ | 4-CH-C(F)(F)-CF(Cl) | O | 219 |

TABLE 1-continued

| Example No. | R¹ | R² | R³ | R⁴ | R⁵ | X | Melting point [°C.] |
|---|---|---|---|---|---|---|---|
| 46 | 4-F | | H | H | 3-CF₃ | 4—CH(—)—C(Cl)(F)—C(F)(F) (2-chloro-3,3,4,4-tetrafluorocyclobutyl) | O | 207 |
| 47 | 4-F₃C—C₆H₄—O— | | H | H | 3-CF₃ | 4—CH(—)—C(Cl)(F)—C(F)(F) | O | 145 |
| 48 | 4-CH₃O— | | H | H | 3-CF₃ | 4—CH(—)—C(Cl)(F)—C(F)(F) | O | 206 |
| 49 | | 3,4-O—CH₂—O— | H | | 3-CF₃ | 4—CH(—)—C(Cl)(F)—C(F)(F) | O | 228 |

Preparation example according to process version (a) for the compound of Example 9

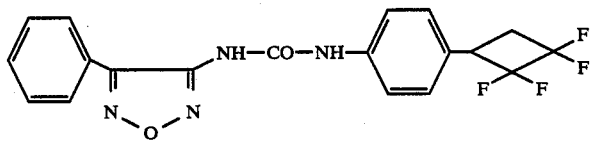

3.22 g (0.02 mol) of 3-amino-4-phenyl-1,2,5-oxadiazole are dissolved in 10 ml of dry dimethylformamide. 5.4 g (0.022 mol) of 4-(2,2,3,3-tetrafluorocyclobut-1-yl-)-phenylisocyanate are added to this solution. The mixture stirred for 6 hours at 100° C., after cooling, the product is precipitated by dropwise addition of water. It is washed several times with water. The product, separated off from the aqueous phase, is covered with toluene: petroleum ether=1:3 and dried at 80° C.

7.9 g (94.5% of theory) of 1-[4-(2,2,3,3-tetrafluorocyclobutyl)-phenyl]-3-(4-phenyl-1,2,5-oxadiazol-3-yl)-urea having a melting point of 206° C. are obtained.

Starting materials of the formula (VI) (A=—NH₂)

Example (VI-1)

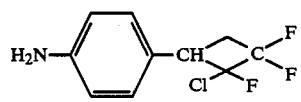

158.0 g of 4-(2-chloro-2,3,3-trifluorocyclobutyl)-nitrobenzene in 400 ml of methanol are placed in a hydrogenation autoclave, 10 g of Raney nickel are added, and the mixture is hydrogenated at 25° C.–40° C. using a hydrogen pressure of 30 bar. The catalyst is subsequently filtered off, the solvent is removed in vacuo, and the residue is distilled.

128 g of 4-(2-chloro-2,3,3-trifluorocyclobut-1-yl)-aniline of boiling point 157–160° C./20 mbar (2000 Pa) are obtained.

The following compounds of the formula (VI) (A=—NH₂) can be obtained in analogy to Example (VI-1):

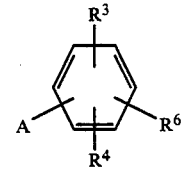

(VI)

Example (VI-2)

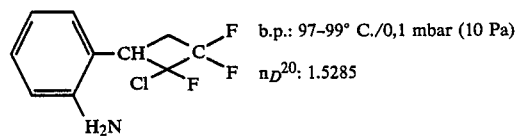

b.p.: 97–99° C./0,1 mbar (10 Pa)
$n_D^{20}$: 1.5285

Example (VI-3)

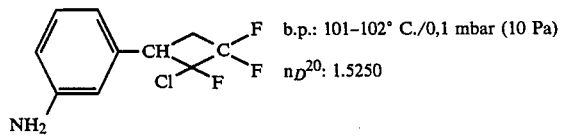

b.p.: 101–102° C./0,1 mbar (10 Pa)
$n_D^{20}$: 1.5250

Example (VI-4)

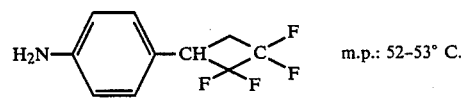

m.p.: 52–53° C.

Example (VI-5)

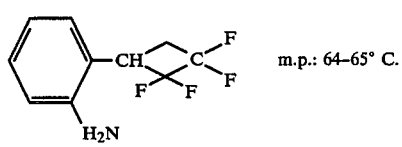

m.p.: 64–65° C.

Example (VI-6)

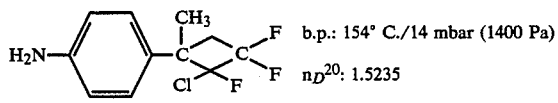

b.p.: 154° C./14 mbar (1400 Pa)
$n_D^{20}$: 1.5235

Example (VI-7)

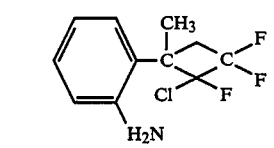

b.p.: 150–151° C./20 mbar (2000 Pa)

$n_D^{20}$: 1.5268

Example (VI-7)

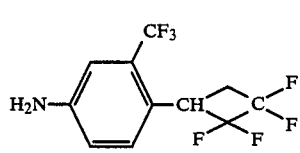

b.p.: 122–124° C./2 mbar (200 Pa)

Example (VI-8)

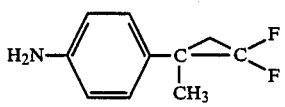

b.p.: 118–120° C./14 mbar (1400 Pa)

$n_D^{20}$: 1.5223

Example (VI-9)

Starting materials of the formula (VI) (A=—NCX)

Example (VI-10)

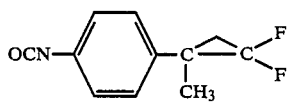

42 g of 4-(2,2-difluoro-1-methylcycloprop-1-yl)-aniline are replaced in 500 ml of chlorobenzene at about 5° C., and 40 g of phosgene are passed in, the temperature being increased. When the boiling point of the solution is reached, the vessel is blown out with nitrogen. The reaction mixture is concentrated and the crude product is purified by distillation.

41 g of 4-(2,2-difluoro-1-methylcycloprop-1-yl)-phenyl isocyanate of boiling point 120° C./16 mbar (1600 Pa) are obtained.

Example (VI-11)

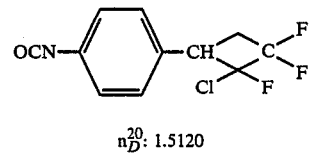

$n_D^{20}$: 1.5120

Example (VI-12)

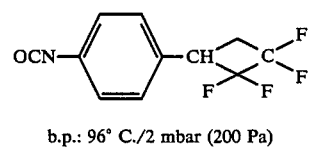

b.p.: 96° C./2 mbar (200 Pa)

$n_D^{20}$: 1.4879

Starting materials of the formula (VII)

Example (VII-1)

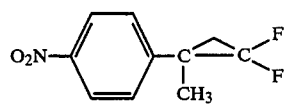

80 g of 2,2-difluoro-1-methyl-1-phenylcyclopropane (preparation, see below) are placed at 5° C. in a nitration apparatus with stirrer and dropping funnel, and a mixture of 50 g of 67% strength nitric acid and 60 g of concentrated sulphuric acid is added dropwise. The mixture is subsequently stirred for one hour at 10° C. and one hour at 20° C., and poured onto ice. The organic phase is separated off, dried and separated.

86 g of crude 4-(2,2-difluoro-1-methylcycloprop-1-yl)-nitrobenzene are obtained.

The following compounds of the formula (VII) can be prepared analogously to Example (VII-1):

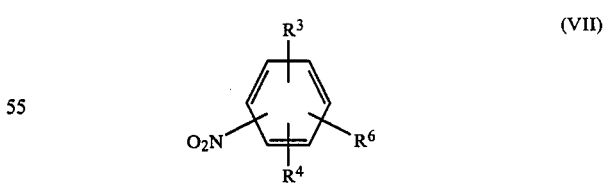

Example (VII-2)

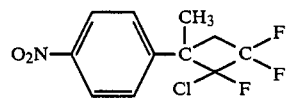

b.p.: 140–146° C./1.5 mbar (150 Pa)

-continued $n_D^{20}$: 1.5195

Example (VII-3)

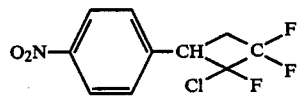

b.p.: 135–138° C./0.2 mbar (20 Pa)

$n_D^{20}$: 1.5200

Example (VII-4)

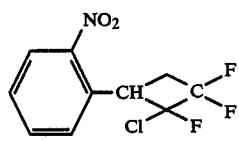

b.p.: 131–132° C./0.15 mbar (15 Pa)

$n_D^{20}$: 1.5230

Example (VII-5)

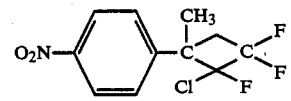

b.p.: 135–137° C./1 mbar (100 Pa)

$n_D^{20}$: 1.590

Example (VII-6)

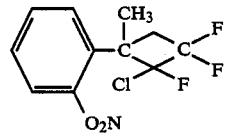

b.p.: 119–120° C./0.2 mbar (20 Pa)

$n_D^{20}$: 1.5215

Example (VII-7)

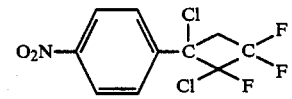

b.p.: 128–130° C./0.8 mbar (20 Pa)
$n_D^{20}$: 1.5480

Example (VII-8)

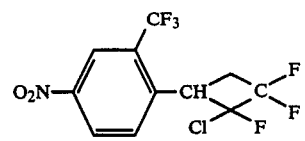

b.p.: 114–118° C./1.4 mbar (140 Pa)
$n_D^{20}$: 1.4865

Preparation of 2,2-difluoro-1-methyl-1-phenylcyclopropane

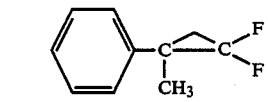

200 g of 1-methyl-styrene, 20 g of tetrabutylammonium chloride and 10 g of hydroquinone are placed in an autoclave, and 500 g of difluorochloromethane are then introduced under pressure, the mixture is heated to 130° C., and 600 g of ethylene oxide are added within one hour. After 12 hours, the reaction mixture is cooled and distilled over a column. The fraction at 53° C.–65° C./14 mbar is washed three times with water, dried and redistilled.

215 g of 2,2-difluoro-1-methyl-1-phenylcyclopropane of boiling point 85° C./14 mbar (1400 Pa) are thus obtained.

The other starting materials of the general formula (VIII) can be obtained analogously.

Use Examples

The following compounds were employed as comparison substances in the following use examples:

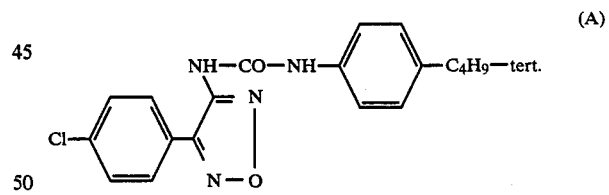
(A)

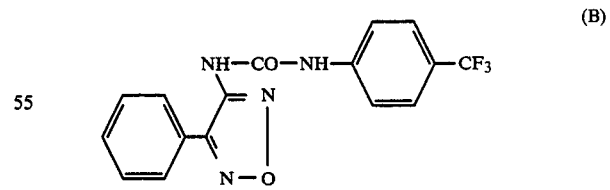
(B)

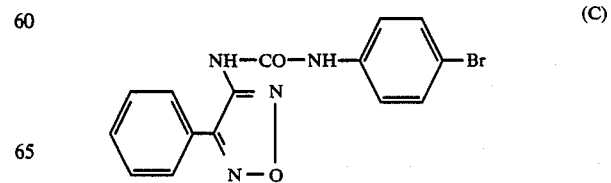
(C)

from EP-A 00,132,680.

Example A

Egg sterility test and development inhibition test with *Tetranychus urticae* (common spider mite)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

The leaves of a bean plant (*Phaseolus vulgaris*) are immersed in the active compound preparation of appropriate concentration. After the preparation of active compound has dried on, the leaves are infested with female spider mites for about 16 hours for eggs to be deposited (about 50 eggs/repeated experiment). The total of sterile and/or destroyed eggs and the destroyed larvae, nymphs and dormant stages of a generation, based on the number of eggs deposited, gives the destruction in %. 100% means that all the mites have been destroyed; 0% means that none of the mites have been destroyed.

In this test, the compounds of Preparation Examples (1), (2), (4), (5), (7), (9), (20), (21), (23) and (24) exhibited an action of 100% after 14 days at an active compound concentration of 0.01%, whereas the comparison compounds (A), (B) and (C) exhibited an action of 62%, 8% and 0% respectively.

Example 8

Phaedon larvae test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated with the preparation of the active compound of the desired concentration. A leaf of the treated plant is placed in a plastic container and infested with larvae (L3) of the mustard beetle (*Phaedon cochleariae*). After 2 to 4 days a further leaf of the same plant is used in each case for subsequent feeding.

After specified periods of time, the destruction in % is determined. 100% means that all the beetle larvae have been killed; 0% means that none of the beetle larvae have been killed.

In this test, the compounds of Preparation Examples (1), (5) and (21), for example, exhibited an action of 100% after 14 days at an exemplary active compound concentration of 0.1%, whereas the comparison compounds (A), (B) and (C) had an action of 10%, 20% and 0% respectively.

It will be understood that the specification and examples are illustrative but not limitative of the present invention and that other embodiments within the spirit and scope of the invention will suggest themselves to those skilled in the art.

We claim:

1. A substituted furazan of the formula

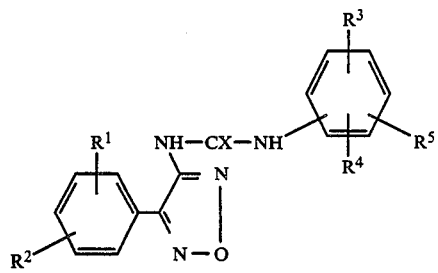

in which
  $R^1$ and $R^2$ are identical or different and represent hydrogen, halogen, $C_1$-$C_6$-alkyl, $C_1$-$C_6$-alkoxy, $C_1$-$C_6$-alkylthio, halogeno-$C_1$-$C_6$-alkyl, halogeno-$C_1$-$C_6$-alkoxy, halogeno-$C_1$-$C_6$-alkylthio or aryloxy, having 6 to 10 carbon atoms in the aryl part, which is optionally substituted by halogen, nitro, cyano, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy and/or halogeno-$C_1$-$C_4$-alkylthio, or
  $R^1$ and $R^2$ together represent $C_1$-$C_3$-alkylene radical which is interrupted by 1 or 2 oxygen atoms or bonded to the phenyl ring via 1 or 2 oxygen atoms and which is optionally substituted by halogen and/or $C_1$-$C_2$-alkyl,
  $R^3$ and $R^4$ are identical or different and represent hydrogen, halogen, $C_1$-$C_6$-alkyl, $C_1$-$C_6$-alkoxy, halogeno-$C_1$-$C_6$-alkyl or halogeno-$C_1$-$C_4$-alkoxy,
  $R^5$ represents cycloalkyl, having 3 to 8 carbon atoms, which is substituted by halogen and/or $C_1$-$C_2$-alkyl, and
  X represents oxygen or sulphur.

2. A substituted furazan according to claim 1, in which
  $R^1$ and $R^2$ are identical or different and represent hydrogen, fluorine, chlorine, bromine, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy, halogeno-$C_1$-$C_4$-alkylthio or phenoxy which is optionally substituted by halogen, nitro, cyano, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy and/or halogeno-$C_1$-$C_4$-alkylthio, or
  $R^1$ and $R^2$ together represent a $C_1$-$C_3$-alkylene radical which is interrupted by 1 or 2 oxygen atoms or bonded to the phenyl ring via 1 or 2 oxygen atoms and which is optionally substituted by fluorine, chlorine and/or methyl,
  $R^3$ and $R^4$ are identical or different and represent hydrogen, fluorine, chlorine, bromine, $C_1$-$C_4$-alkyl, $C_1$-$C_4$-alkoxy, halogeno-$C_1$-$C_4$-alkyl or halogeno-$C_1$-$C_4$-alkoxy, and
  $R^5$ represents cycloalkyl, having 3 to 6 carbon atoms, which is substituted by fluorine, chlorine, bromine, and/or methyl.

3. A substituted furazan according to claim 1, in which
  $R^1$ and $R^2$ are identical or different and represent hydrogen, fluorine or chlorine,
  $R^2$ and $R^3$ represent hydrogen, and
  $R^5$ represents 2-chloro-2,3,3-trifluorocyclobutyl, 1-methyl-2-chloro-2,3,3-trifluorocyclobutyl or 2,2,3,3-tetrafluorocyclobutyl.

4. A compound according to claim 1, wherein such compounds is 1-[4-(2-chloro-2,3,3-trifluorocyclobutyl)- phenyl]-3-(4-phenyl-1,2,5-oxadiazol-3-yl)-urea of the formula

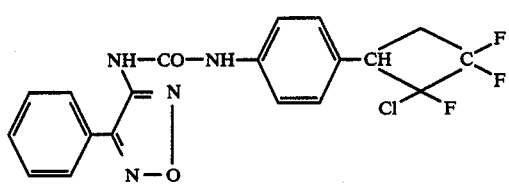

5. A compound according to claim 1, wherein such compound is 1-[4-(2-chloro-2,3,3-trifluorocyclobutyl)-phenyl]-3-(4-p-fluorophenyl-1,2,5-oxadiazol-3-yl)-urea of the formula

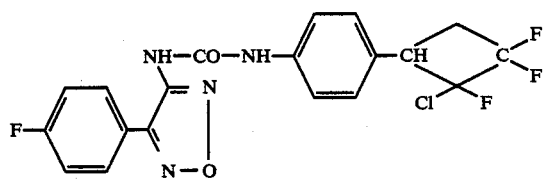

6. A compound according to claim 1, wherein such compound is 1-[4-(2-chloro-1-methyl-2,3,3-trifluorocyclobutyl)-phenyl]-3-(4-p-fluorophenyl-1,2,5-oxadiazol-3-yl)-urea of the formula

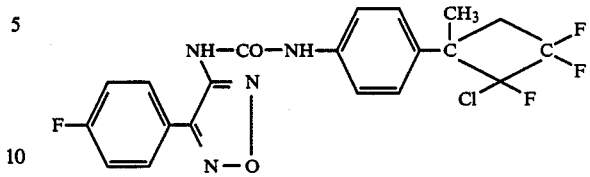

7. An insecticidal or acaricidal composition comprising an insecticidally or acaricidally effective amount of a compound according to claim 1 and a diluent.

8. A method of combating insects or acarids which comprises applying to such insects or acarids or to an insect or acarid habitat an insecticidally or acaricidally effective amount of a compound according to claim 1.

9. The method according to claim 8, wherein such compound is
1-[4-(2-chloro-2,3,3-trifluorocyclobutyl)-phenyl]-3-(4-phenyl-1,2,5-oxadiazol-3-yl)-urea
1-[4-(2-chloro-2,3,3-trifluorocyclobutyl)-phenyl]-3-(4-p-fluorophenyl-1,2,5-oxadiazol-3-yl)-urea or
1-[4-(2-chloro-1-methyl-2,3,3-trifluorocyclobutyl)-phenyl]-3-(4-p-fluorophenyl)1,2,5-oxadiazol-3-yl)-urea.

* * * * *

UNITED STATES PATENT AND TRADEMARK OFFICE
CERTIFICATE OF CORRECTION

PATENT NO. : 4,853,397
DATED : August 1, 1989
INVENTOR(S) : Wilhelm Sirrenberg, et al It is certified that error appears in the above-identified patent and that said Letters Patent is hereby corrected as shown below:

| | |
|---|---|
| Title Page, under "Foreign Patent Documents, line 2 | Insert --European Patent Office-- |
| Abstract, line 1 after first formula | Delete "n" and substitute --in-- |
| Col. 3, line 26 | Correct spelling of --halogenoalkyl-- |
| Col. 3, line 26 | Correct spelling of --halogenoalkylthio-- |
| Col. 3, line 35 | Delete "R2" and substitute --$R^2$-- |
| Col. 4, line 64 | Delete "vis" and substitute --via-- |
| Col. 5, line 12 | Delete "sec.-butyl," second instance |
| Col. 6, line 40 | Delete "I" and substitute --If-- |
| Col. 6, line 66 | Delete "staring" and substitute --starting-- |
| Col. 9, line 29 | Delete "150" and substitute --130-- |
| Col. 9, line 51 | End of line delete "of" and substitute --or-- |
| Col. 23, line 32 | Delete "(VI-7)" and substitute --(VI-8)-- |
| Col. 23, line 43 | Delete "(VI-8)" and substitute --(VI-9)-- |
| Col. 23, line 55 | Delete "Example (VI-(9)" |
| Col. 23, line 66 | Delete "replaced" and substitute --placed-- |
| Col. 27, line 33 | Delete "Example 8" and substitute --Example B-- |

UNITED STATES PATENT AND TRADEMARK OFFICE
CERTIFICATE OF CORRECTION

PATENT NO. : 4,853,397
DATED : August 1, 1989
INVENTOR(S) : Wilhelm Sirrenberg et al It is certified that error appears in the above-identified patent and that said Letters Patent is hereby corrected as shown below:

Col. 28, line 24        After "represents" insert
                        --a--
Col. 28, line 68        Delete "compounds" and substitute
                        --compound--

Signed and Sealed this

Fourth Day of December, 1990

Attest:

HARRY F. MANBECK, JR.

*Attesting Officer*            *Commissioner of Patents and Trademarks*